United States Patent
Dalloro et al.

(10) Patent No.: US 6,949,687 B2
(45) Date of Patent: Sep. 27, 2005

(54) PROCESS FOR THE PRODUCTION OF MESITYLENE AND DURENE

(75) Inventors: Leonardo Dalloro, Bollate (IT);
Alberto Cesana, Carate Brianza (IT);
Roberto Buzzoni, San Mauro Torinese (IT); Franco Rivetti, Milan (IT);
Caterina Rizzo, San Donato Milanese (IT); Virginio Arrigoni, Milan (IT);
Carlo Perego, Carnate (IT)

(73) Assignees: Polimeri Europa S.p.A., Brindisi (IT);
Enitecnologie S.p.A., San Donato Milanese (IT)

(*) Notice: Subject to any disclaimer, the term of this patent is extended or adjusted under 35 U.S.C. 154(b) by 0 days.

(21) Appl. No.: 10/736,594

(22) Filed: Dec. 17, 2003

(65) Prior Publication Data

US 2004/0127762 A1 Jul. 1, 2004

(30) Foreign Application Priority Data

Dec. 20, 2002 (IT) .................................... MI2002A2704

(51) Int. Cl.[7] ................................................ C07C 5/22
(52) U.S. Cl. ...................................... 585/481; 585/475
(58) Field of Search ................................. 585/481, 475

(56) References Cited

U.S. PATENT DOCUMENTS 3,637,880 A   1/1972   Burress
5,043,512 A   8/1991   Chu et al.
5,206,194 A   4/1993   Clark
5,929,295 A * 7/1999   Wu et al. .................... 585/475

FOREIGN PATENT DOCUMENTS

FR           2.140.738        1/1973

OTHER PUBLICATIONS

An Nan Ko, et al., "Isomerization and Disproportionation of 1,2,4–trimethylbenzene Over Hy Zeolite", Journal of the Chinese Chemical Society, AN 1994:247768, XP–002299017, 1994, pp. 1–2.

* cited by examiner

Primary Examiner—Thuan D Dang
(74) Attorney, Agent, or Firm—Oblon, Spivak, McClelland, Maier & Neustadt, P.C.

(57) ABSTRACT

A process is described for the contemporaneous preparation of mesitylene and durene, characterized in that mesitylene and durene are obtained exclusively starting from pseudo-cumene without the use of any further chemical compound, operating in continuous, at a temperature ranging from 210 to 400° C., at a pressure ranging from 1 to 50 bar, with a weight space velocity ranging from 0.1 to 20 hours$^{-1}$ and in the presence of a catalyst based on crystalline metal-silicates in acid form. After the recovery of mesitylene and durene from the reaction raw product, some of the remaining components of the raw product itself are recycled and fed to the reactor together with the pseudo-cumene.

24 Claims, 1 Drawing Sheet

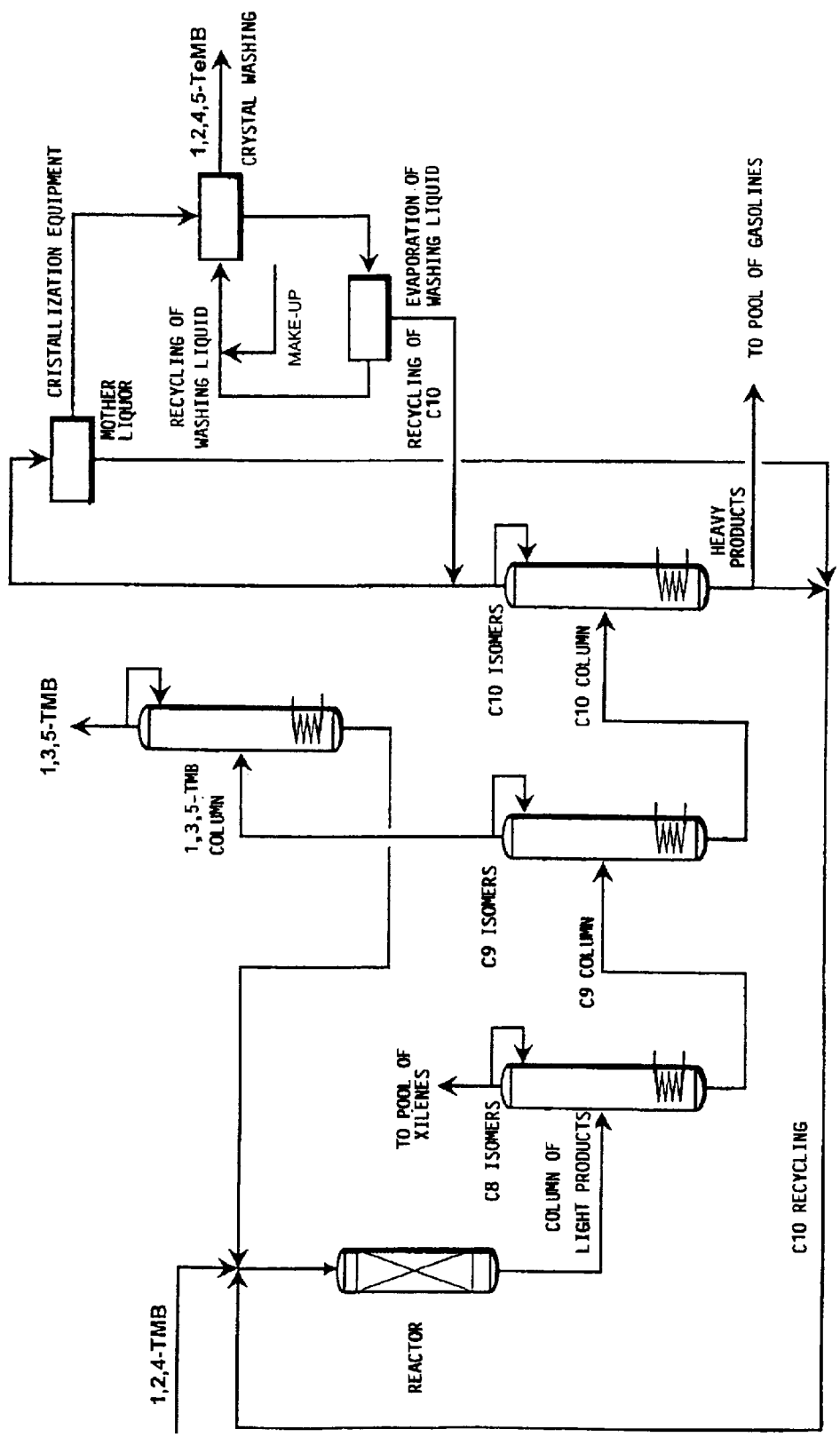
Fig. 1 PLANT SCHEME

PROCESS FOR THE PRODUCTION OF MESITYLENE AND DURENE

The present invention relates to a process for the contemporaneous preparation of mesitylene (1,3,5-trimethylbenzene) and durene (1,2,4,5-tetramethylbenzene) starting from pseudo-cumene (1,2,4-trimethylbenzene), without the use of any further chemical compound.

More specifically, the present invention relates to a continuous process, in which the chemical transformation is carried out in the presence of a catalyst based on crystalline metal-silicates in acid form.

Mesitylene and durene are chemical intermediates, mainly used for the preparation of benzenepolycarboxylic acids, trimesic acid (or 1,3,5-benzenetricarboxylic acid) and pyromellitic acid (or 1,2,4,5-benzenetetracarboxylic acid), respectively; pseudo-cumene, from which trimellitic acid (or 1,2,4-benzenetricarboxylic acid) is obtained, has an analogous use. These compounds, possibly in form of anhydride, are, in turn, used in the production of plasticizers for polymers and polyimide, epoxy and polyester resins.

Pseudo-cumene is obtained by distillation from reforming hydrocarbon streams, in which it is present in a high concentration.

The same method cannot be applied for the recovery of mesitylene and durene as the process is not sufficiently advantageous and it is therefore necessary to use alternative technologies.

In particular, the recovery of mesitylene is made critical by the presence of other components of the reforming mixture having very similar volatilities, above all the three isomers of ethyl-methylbenzene and mainly 2-ethyl-methylbenzene. The problem also arises for the recovery of durene, whose physico-chemical characteristics are extremely similar to those of its isomers, and in this case the difficulties are even greater due to its low concentration in the reforming mixture.

The alternative technologies are based on chemical reactions.

Mesitylene can be obtained by the dehydration and condensation of acetone on catalysts based on tantalum (GB 852,674) or on niobium (U.S. Pat. No. 5,087,781, GB 931,893); the process produces high concentrations of mesitylene, but uses three molecules of reagent for each molecule of mesitylene produced and can only be advantageous for producers having low-cost acetone at their disposal.

U.S. Pat. Nos. 2,873,300, 3,189,659 and 3,987,120 describe the recovery of mesitylene from reforming hydrocarbon streams based on sulfonation processes with concentrated sulfuric acid. These processes have a limited industrial use due to the formation of considerable quantities of acid by-products.

U.S. Pat. No. 2,589,621 describes the preparation of mesitylene from a trimethylbenzene isomer such as pseudo-cumene by means of isomerization in liquid phase in the presence of HF and $BF_3$. This process suffers from the use of an extremely corrosive and dangerous catalytic system.

U.S. Pat. No. 3,253,049 describes the production of mesitylene from pseudo-cumene by means of isomerization effected on a catalyst based on platinum supported on alumina containing chlorine, in the presence of hydrogen in order to limit phenomena of coke formation. This process suffers from the use of hydrogen and the use of a catalyst containing a noble metal such as platinum.

U.S. Pat. No. 3,637,880 describes a process for the preparation of mesitylene starting from hydrocarbon mixtures of xylenes and pseudo-cumene, carried out in the presence of crystalline alumino-silicates.

U.S. Pat. No. 5,004,854 describes a process for recovering pseudo-cumene and mesitylene from a $C_9$ aromatic cut containing propylbenzenes and ethylmethylbenzenes by a treatment with hydrogen in the presence of a zeolite having a Si/Al ratio of at least 12 and a constraint index ranging from 1 to 12 so as to convert the propylbenzenes and ethylmethylbenzenes and form a mixture of products containing benzene, toluene, $C_8$-$C_9$-$C_{10}$ alkylbenzenes, from which mesitylene and pseudo-cumene can be recovered. The catalyst is preferably a ZSM-5 containing a metal with a hydrogenating function such as platinum, nickel, molybdenum, cobalt or zinc. This process also suffers from the use of hydrogen and the use of a catalyst containing a metal with a hydrogenating function.

U.S. Pat. No. 3,219,720 describes the preparation of durene by the isomerization of polymethylbenzenes in the presence of $AlCl_3$. This process suffers from the use of a corrosive and dangerous catalytic system and the co-production of waste products.

U.S. Pat. No. 3,636,177 describes the preparation of durene from tetramethylbenzene isomers such as isodurene and prenitene by isomerization in liquid phase in the presence of HF and $BF_3$. This process suffers from the use of an extremely corrosive and dangerous catalytic system.

Durene can be most commonly obtained by the alkylation of benzene or other methyl derivatives of benzene, optionally in a mixture, containing from 1 to 3 methyl groups, using suitable alkylating agents, among which mainly methyl alcohol, but also dimethylether or methyl chloride and catalysts based on supported aluminum trichloride, silver, boria, phosphorous pentoxide or chromium sesquioxide and crystalline aluminum-silicates.

U.S. Pat. No. 3,326,997, for example, describes a process for the production of durene starting from methylbenzenes containing from 2 to 3 methyl groups in the presence of a methylating agent such as methanol on an acid silica mobile bed.

U.S. Pat. Nos. 4,520,219 and 4,891,467 describe a process in which, starting from benzene or methylbenzenes such as xylenes and methanol or dimethylether and with a catalyst based on borosilicates or fluoro-borosilicates, durene is obtained as main product together with significant quantities of pseudo-cumene.

Other patents claim the preparation of durene starting exclusively from methanol or its synthesis gas precursor.

For example, U.S. Pat. No. 3,894,105 describes a process for the conversion of methanol to durene in the presence of a zeolite with a Si/Al ratio of at least 12 and a constraint index ranging from 1 to 12, for example a ZSM-5, operating at high pressure.

U.S. Pat. No. 4,524,228 describes a process for producing durene in which oxygenated derivatives of synthesis gas, such as mixtures of methanol and dimethylether are reacted in the presence of a zeolite, preferably ZSM-5, obtaining a gasoline from which durene is separated by fractionation and crystallization.

These processes also have disadvantages: a first problem relates to the availability of methanol, which cannot always be found in plants dedicated to the exploitation of oil fractions, these processes, moreover, also create problems of a technological nature. One of the main drawbacks concerns the selectivity as it is not at all easy to control the desired alkylation degree, with the formation of by-products which cannot always be conveniently used. Furthermore, when materials based on zeolites are used as catalysts, another disadvantage derives from the fact that the considerable quantities of water formed in the reaction tend to irreversibly deactivate the catalyst, reducing its life. This in fact limits the use of zeolitic structures, limiting the selection of the catalyst from those which have a sufficiently prolonged life in the presence of water at high temperatures and making it necessary to renounce the use of structures with a poor resistance.

The process, object of the present invention, comprises the contemporaneous chemical transformation of pseudo-cumene into mesitylene and durene with a catalyst based on crystalline metal-silicates (zeolites) in acid form and the recovery of the two compounds from the reaction raw product formed. The production of mesitylene and durene therefore takes place exclusively starting from pseudo-cumene without the use of any further chemical compound and, surprisingly, without any substantial formation of coke, thus allowing to work at constant catalytic activity for extremely long operating cycles.

The zeolites are used in their acid or prevalently acid form, i.e. with all or most of the sites originally occupied by cations which are substituted by hydrogen ions. The substitution can, for example, be conveniently effected by means of exchange with ammonium ions and subsequent calcination, as is well known in the state of the art.

For the purposes of the process, object of the invention, zeolites characterized by a spaciousness index equal to or greater than 3, are adopted; those characterized by a spaciousness index greater than 5, are particularly preferred. The spaciousness index is a parameter which provides a real measurement of the pore width of materials such as zeolites and is described in "Zeolites and Related Microporous Materials: state of art 1994", Studies in Surface Science and Catalysis, vol.84 (1994), page 37 onwards.

For illustrative purposes, Table 1 below indicates some of the spaciousness index values:

TABLE 1

Spaciousness index values

| Zeolite | Spaciousness index |
| --- | --- |
| Y | 21 |
| ZSM-20 | 21 |
| Beta | 19 |
| L | 17 |
| MCM-22 (=ERB-1) | 8 |
| Mordenite | 7 |
| ERS-10 | 5.3 |
| Nu-1 | 5 |
| Offretite | 5 |
| ZSM-12 | 3 |
| ZSM-5 | 1 |
| ZSM-22 | 1 |

Zeolites which can be used in the process of the present invention are beta zeolite, Y zeolite, ZSM-12, MCM-22, ERB-1, mordenite, offretite, L zeolite, mazzite, ERS-10, Nu-1, ZSM-20 and Nu-88.

In particular, beta zeolite, described for the first time in U.S. Pat. No. 3,308,069, has the formula:

$$[(x/n)M(1\pm0.1-x)Z]AlO_2 \cdot y\,SiO_2 \cdot w\,H_2O$$

wherein x is less than 1, preferably less than 0.75, y varies from 5 to 100, w varies from 0 to 4, M is a metal of group IA, IIA and IIIA or a transition metal, n is the valence of M, Z is hydrogen, ammonium ion or organic cation.

Modifications of beta zeolites can be used in the process of the present invention, obtained by the partial or total isomorphous substitution of the aluminum of the zeolite with boron, iron or gallium, described in BE 877,205 877,205 and EP 55,046, and beta zeolite containing controlled quantities of sodium, potassium, calcium or nickel described in EP 629,599.

Y zeolite is described for the first time in U.S. Pat. No. 3,130,007.

MCM-22 is described for the first time in U.S. Pat. No. 4,954,325 and ERB-1 is described for the first time in EP 293,032.

The mazzite zeolite is described in U.S. Pat. No. 3,578,723 and U.S. Pat. No. 4,021,447.

The zeolite Nu-88 is described in EP 825,152 and in Belgian patent application 2001/0808.

ZSM-12 zeolite is described in U.S. Pat. No. 3,832,449.

The zeolite Nu-1 is described in U.S. Pat. No. 4,060,590.

Offretite is described in J. M. Bennett et al., Nature 214, 1005 (1967).

ZSM-20 zeolite is described in U.S. Pat. No. 3,972,983.

The zeolite ERS-10 is described in EP 796,821.

The zeolite mordenite is described in U.S. Pat. No. 4,503,023.

L zeolite is described in U.S. Pat. No. 3,216,789.

Reference to the previous zeolitic structures is also made in "Atlas of Zeolite Framework Types", Ch. Baerlocher, W. M. Meier and D. H. Olson, Fifth Revised Edition 2001, El-sevier Amsterdam.

Beta zeolite is preferably used.

With respect to the chemical composition, zeolites which are particularly suitable for the process of the present invention are those with a molar ratio $SiO_2/Al_2O_3$ which ranges from 4.5 to 4,000, preferably from 4.5 to 400.

The process, object of the invention, is carried out at a temperature ranging from 210 to 450° C. and preferably from 225 to 400° C. The process is carried out at a pressure ranging from 1 to 50 bars, preferably in liquid phase at a pressure generally ranging from 5 to 50 bar.

The feeding consists of pure pseudo-cumene or, as can be seen hereunder, in a mixture with various recycled compounds deriving from the same process. The feeding flow-rate is suitably selected, in a combination with other process variables, in relation to the conversion degree desired. A space velocity (WHSV=Weight Hourly Space Velocity, expressed in kg of hydrocarbon mixture/hour/kg of catalyst) ranging from 0.1 to 20 hours$^{-1}$, can be used for the feeding.

The process is preferably carried out in continuous in a fixed bed reactor and, as the enthalpy of the process is not particularly high, no particular heat exchange expedients are required, and what is generally known as an industrial adiabatic reactor is therefore adequate.

In this case, the zeolitic material which constitutes the catalyst must be conveniently formed by mixing, with suitable techniques, the active phase, consisting of the crystal in powder form of the pre-selected zeolite, with an inorganic binder which is sufficiently inert with respect to the reagents and products, for example silica, alumina, zirconia, magnesia or their mixtures. Alumina is the preferred binder. The ratio between active phase, consisting of the zeolite, and the binder can be kept within a ratio of 5:95 to 95:5 w/w, preferably from 20:80 to 80:20 w/w.

The forming is effected by means of processes well known in the state of the art, for example by means of an extrusion process. The formed catalyst thus obtained can be in various forms, in order to obtain a low pressure drop and suitable mechanical and abrasion resistance.

When beta zeolite is selected as active phase, the forming processes of the catalyst described in patents EP 687,500 and EP 847,802, are particularly preferred.

According to these processes, the beta zeolite is prepared in the form suitable for industrial use with an inorganic binder, in particular the catalyst described in EP 687,500 is characterized by an extrazeolitic porosity, i.e. the porosity obtained by summing the mesoporosity and the macroporosity of the catalytic composition itself, consisting of a fraction of at least 25% of pores with a radius higher than 100 Å.

The catalyst described in EP 847,802 comprising a beta zeolite bound with an inorganic binder, having an extrazeolitic porosity consisting of a fraction of at least 25% of pores with a radius higher than 100 Å, is also characterized by a total volume of extrazeolitic pores greater than or equal to 0.80 ml/g.

With the catalysts and under the operating conditions described above, the catalytic activity can be maintained for prolonged periods (several thousands of hours), without requiring any particular interventions or operating procedures for re-establishing the catalytic activity. In particular, it is not necessary to adopt those methods disclosed in the state of the art for maintaining the catalytic activity for long periods of time, such as impregnation of the catalyst with metals typically used for hydrogenation reactions (such as Ni, Pt, etc.) and the addition of hydrogen to the reaction mixture, as described for example in U.S. Pat. No. 4,891,467.

The duration of the catalytic activity can be prolonged by gradually increasing the process temperature, for example by 2–4° C. every 100 hours of processing. Subsequently, when the catalyst begins to show at least partial deactivation, the duration of the catalytic activity can be further prolonged by effecting processing periods at a temperature at least 40° C. higher than that at which the catalyst starts demonstrating signs of deactivation and for a time ranging from 100 to 300 hours. In this period, there is a substantial rejuvenation of the catalyst after which the previous temperature conditions can be re-established. This rejuvenation treatment can be cyclically repeated to maximize the benefits.

The catalyst can in any case be subjected to regeneration treatment: the most suitable method is by combustion of the carbonaceous deposits accumulated in the period of use, according to what is known in the state of the art, operating for example at a temperature ranging from 450 to 550° C., at a pressure ranging from 1 to 3 bar, with mixtures of oxygen and nitrogen in a ratio ranging from 0.1 to 20% by volume and with a space velocity (GHSV=Gas Hourly Space Velocity, expressed in 1 of gas mixture/hour/l of catalyst) ranging from 3000 to 6000 hours$^{-1}$. Considering the low regeneration frequency, the regeneration does not have to be effected in the same reactor in which the catalyst is charged for the reaction, the catalyst can be discharged during the periodic maintenance phases of the plant and regenerated elsewhere; in this way the reactor can be constructed without control devices necessary for effecting the regeneration.

There are two types of reactions which take place in the process, object of the invention, isomerization reactions and transalkylation reactions.

The isomerization of pseudo-cumene leads to the formation of mesitylene and hemimellitene (1,2,3-trimethylbenzene); a mixture of three trimethylbenzene isomers is therefore generated, hereunder called "$C_9$ isomers", for the sake of brevity.

The transalkylation of the $C_9$ isomers leads to the formation of a mixture of the three isomers of tetramethylbenzene, durene, isodurene (1,2,3,5-tetramethylbenzene) and prenitene (1,2,3,4-tetramethylbenzene), hereunder called "$C_{10}$ isomers", and, at the same time, a mixture of the three isomers of dimethylbenzene, ortho-xylene (1,2-dimethylbenzene), meta-xylene (1,3-dimethylbenzene) and para-xylene (1,4-dimethylbenzene), hereunder called "$C_8$ isomers".

Although the production is effected starting from pseudo-cumene alone, as described below, some of the hydrocarbons produced by the process itself can also be optionally fed together with the pseudo-cumene, which are recycled after separation from the reaction raw product of the two compounds of interest. Analogously to the pseudo-cumene, the recycled trimethylbenzenes and tetramethylbenzenes undergo both isomerization and transalkylation, to generate mesitylene and durene.

According to a preferred embodiment of the invention, a fraction of light compounds is separated by distillation from the reaction raw product, $C_8$ isomers, an intermediate fraction also containing non-converted pseudo-cumene, $C_9$ isomers, a heavier intermediate fraction, $C_{10}$ isomers, and a residue is left, containing a part of $C_{10}$ isomers together with small quantities of pentamethylbenzene and hexamethylbenzene.

The mesitylene is recovered from the mixture of $C_9$ isomers by distillation at a purity suitable for industrial use (>99%), whereas the remaining part of $C_9$ isomers (essentially hemimellitene and pseudo-cumene) is recycled to the process itself.

The durene is recovered from the mixture of $C_{10}$ isomers by crystallization at a purity suitable for industrial use (>99%), whereas the remaining part of $C_{10}$ isomers (essentially isodurene and prenitene) is recycled. The crystallization is carried out with conventional methods, for example without a solvent at a temperature ranging from −20 to 10° C. The raw crystals can then be purified by means of washings with alcohols or light hydrocarbons.

As far as the fraction of $C_8$ isomers is concerned, this is not recycled to the process itself, but according to the requirements of a petrochemical plant, which is dedicated to the exploitation of reforming streams, it is integrated in the stream of xylenes.

The distillation residue of the raw product is sent to the stream of fuels.

FIG. 1 shows a possible scheme, according to what is specified above, of the process, object of the invention. In this figure 1,2,4-TMB is the pseudo-cumene which feeds the reactor (reactor). The column of light products is the distillation column which separates the $C_8$ isomers, for recovering them from the reaction raw product and sending them to the pool of xylenes. The $C_9$ column is the distillation column which separates the $C_9$ fraction from the remaining part of the reaction raw material; the 1,3,5-TMB column is the distillation column which separates the mesitylene (1,3,5-TMB) from the remaining $C_9$ isomers, which are recycled to the reactor. The C10 column is the distillation column which separates the $C_{10}$ isomers from the residue (heavy products); the $C_{10}$ isomers are sent to the crystallizer, in which the durene, crystallized from the mother liquor, consisting of the remaining $C_{10}$ isomers, is separated. The crystallized durene is purified by washing with a solvent and recovered (1,2,4,5-TeMB); the washing liquid, after evaporation and recycling of the solvent, is recycled to the crystallizer. The mother liquor is recycled to the reactor together with part of the residue of the C10 column. The remaining part of the residue of the C10 column is recovered as fuel (sent to the pool of gasolines).

As described and illustrated hereunder, a characterizing element of the process is the possibility of regulating, in relation to the process requirements, the ratio of the two compounds of interest, by acting on the operating conditions, in particular the temperature.

A further characterizing element of the process is to operate exclusively with mixtures of methyl derivatives of benzene. Unlike what is verified when mixtures having a more complex composition are re-arranged, the opportunity of operating exclusively with methyl derivatives of benzene provides benefits in all the process phases, in particular those concerning the purification of the products, as the number of benzene derivatives is much more limited and the fractionation of the reaction raw product much simpler. In particular, in the absence of benzene derivatives such as ethylmethylbenzenes, the separation and purification of mesitylene by distillation of the $C_9$ cut, is greatly simplified. The separation and purification of durene from the $C_{10}$ cut of the reaction raw product, is also simplified and can be obtained with the conventional crystallization technologies.

Finally, it should be noted that the method adopted is that with which it is possible to operate with the highest concentration of compounds of interest and to reduce the dimensions of the reactor and other plant equipment to the minimum, a significant advantage considering that the reactions in question are already jeopardized by all being equilibrium reactions.

Some illustrative examples are provided for a better understanding of the present invention but should in no way be considered as limiting the scope of the invention itself.

PREPARATION EXAMPLES OF THE CATALYSTS

Example 1—Synthesis of Beta Zeolite

A catalyst based on Beta zeolite was prepared according to the indications provided in the patent EP 847,802, in particular following the instructions of Example 3. A beta zeolite was thus obtained in ammonia form, as crystalline powder, having a molar ratio $SiO_2/Al_2O_3=25$. This form was subsequently transformed in acid form, making it suitable for use in a reactor with the process described in Example 15 of the present patent application.

In the examples specifying the results of the catalytic activity obtained with this catalyst, it is indicated with the name Beta zeolite/100.

Example 2—Synthesis of Beta Zeolite in Industrial Size

A zeolite-based catalyst in acid form (H-Beta) and industrial size was prepared following the indications provided in the patent EP 847,802. In particular, for the preparation of Beta zeolite in crystalline powder form, the instructions of Example 3 of EP 847,802 were followed (exactly as in Example 1 of the present invention) and for the subsequent forming in industrial size, the instructions of Example 4 of EP 847,802 were followed. In this catalyst in pellet form, the concentration of the active phase is 50% by weight and for use in a laboratory reactor, the catalyst was ground to a size of 14–35 mesh.

In the examples specifying the results of the catalytic activity obtained with this catalyst, it is indicated with the name Beta zeolite/50.

Example 3—Synthesis of ZSM-12

185 grams of tetra-ethylammonium hydroxide at 40% by weight, in aqueous solution, are added to 100 grams of demineralized water. 4 grams of sodium aluminate at 56% by weight of $Al_2O_3$, are subsequently added. The limpid solution thus obtained is poured, under stirring, into 500 grams of Ludox HS 40 colloidal silica. After brief stirring, a limpid, homogeneous gel is obtained, which is poured into a 1 litre AISI 316 steel autoclave, equipped with an anchor stirrer. The gel is left to crystallize under hydrothermal conditions at 160° C. for 60 hours.

At this point the autoclave is cooled. The slurry obtained is homogeneous, with a latescent appearance.

The slurry is centrifuged. The solid discharged is washed by redispersion in water, re-centrifuged, dried at 120° C. for 2 hours and calcined at 550° C. for 5 hours. Upon X-ray diffraction analysis, the solid obtained consists of pure ZSM-12.

The solid obtained is exchanged into ammonia form by means of treatment with a solution of ammonium acetate according to the known art. At the end, the product is filtered, repeatedly washed with demineralized water, dried at 120° C. Upon subsequent calcination at 550° C. for 5 hours, the zeolite is obtained in acid form.

Example 4—Synthesis of NU-88

40.70 grams of a solution at 46.8% by weight of N,N-penta-methylene-bis-[N-methyl-3-hydroxy-piperidine]-dihydroxide, are added at room temperature and under magnetic stirring to a solution consisting of 112.96 grams of demineralized water and 1.52 grams of sodium hydroxide. 4.78 grams of $Al_2(SO_4)_3.16H_2O$ and 22.80 grams of $SiO_2$ Sylobloc 47, are added in sequence to the alkaline solution thus obtained.

The reaction mixture is charged into a steel autoclave and placed in an oven to crystallize under autogenous conditions for 14 days at 145° C., subjected to a rotating movement. After cooling to room temperature, the crystalline product is separated from the mother liquor by means of filtration, washed with demineralized water and dried at 120° C. for 2 hours. Analysis of the diffraction spectrum reveals the formation of a pure crystalline phase, the same as that called NU-88.

The sample is then calcined at 550° C. for 5 hours in a stream of air. The zeolite is exchanged into ammonia form by treatment with a solution of ammonium acetate according to the known art. At the end, the product is filtered, repeatedly washed with demineralized water, dried at 120° C. Upon subsequent calcination at 550° C. for 5 hours, the zeolite is obtained in acid form.

Example 5—Synthesis of Mazzite 14.6 grams of tetramethylammonium hydroxide at 25% by weight, in aqueous solution, are added to 139 grams of demineralized water. 4.5 grams of sodium hydroxide and 15.6 grams of sodium aluminate at 54% by weight of $Al_2O_3$, are then added.

100 grams of Ludox HS 40 colloidal silica are poured, under stirring, into the limpid solution thus obtained. After brief stirring, a homogeneous suspension is obtained, and the reaction mixture is charged into a steel autoclave and placed in an oven to crystallize under autogenous conditions for 48 hours at 130° C., subjected to an oscillating movement. After cooling to room temperature, the crystalline product is separated from the mother liquor by means of filtration, washed with demineralized water, dried at 120° C. for 2 hours and calcined at 550° C. for 5 hours.

The solid obtained is exchanged into acid form, by re-dispersion in a solution of demineralized water and ammonium acetate, as described in the known art.

Analysis of the diffraction spectrum reveals the formation of mazzite as pure crystalline phase.

Example 6—Synthesis of MCM-22

619.8 grams of demineralized water, 3.22 grams of sodium hydroxide and 4.60 grams of sodium aluminate at 56% by weight of $Al_2O_3$, are charged into a 1000 ml three-neck flask, equipped with a mechanical stirrer. 26.48 grams of hexamethylene-imine and 45.98 grams of fumed silica (Aerosil 200), are added under constant stirring. The solution is left at reflux temperature for 1 hour under stirring, is then slowly cooled and left in static aging for 15 hours. The suspension is poured into a 1 litre AISI 316 steel autoclave, equipped with an anchor stirrer. The gel is left to crystallize under hydrothermal conditions at 150° C. for 11 days.

At this point, the autoclave is cooled and the solid phase is separated from the mother liquor by means of filtration, washed with demineralized water and dried at 120° C. for 2 hours. Analysis of the diffraction spectrum reveals the formation of a pure crystalline phase of MCM-22.

The sample is then calcined at 550° C. for 5 hours in a stream of air. The zeolite is exchanged in ammonia form by treatment with a solution of ammonium acetate according to the known art. At the end, the product is filtered, repeatedly washed with demineralized water, dried at 120° C. Upon subsequent calcination at 550° C. for 5 hours, the zeolite is obtained in acid form.

Example 7—Synthesis of ERS-10

2.64 grams of sodium hydroxide and 2.82 grams of aluminum isopropylate are dissolved in 360.5 grams of demineralized water; 52.10 grams of an aqueous solution at 45.7% by weight of 6-azoniaspiro[5.5]undecane hydroxide, are then added. 54.26 grams of an aqueous solution of sulfuric acid at 7.5% by weight are subsequently added. 144.84 grams of tetra-ethylorthosilicate are poured, under stirring, into the limpid solution thus obtained. The mixture is moderately heated to favour hydrolysis. After 1 hour, the reaction mixture is discharged into a 1 litre, AISI 316 steel autoclave, equipped with an anchor stirrer. The gel is left to crystallize under hydrothermal conditions at 155° C. for 14 days.

After cooling to room temperature, the crystalline product is separated from the mother liquor by means of filtration, washed with demineralized water, dried at 120° C. for 2 hours and calcined at 550° C. for 5 hours.

The solid obtained is exchanged in acid form, by re-dispersion in a solution of demineralized water and ammonium acetate, according to what is described in the known art.

Analysis of the diffraction spectrum reveals the formation of ERS-10 as pure crystalline phase.

Examples 8–13—Commercial Catalysts

In the activity examples of the present patent application, catalysts based on Y zeolite or mordenite were also tested. In particular, the commercial catalysts indicated in Table 2 below, were used.

This table, in addition to the commercial name of the product adopted, also provides a brief description of the characteristics of the product itself, and the treatment to which each of them was subjected before being used in the reaction. Some of these catalysts, in fact, are already supplied in acid form, but do not have the suitable size for use in a reactor, whereas in other cases catalysts are used in powder and/or salified form with ammonium, which before being used in the reaction were subjected to one of the types of treatment specified in the following examples 14 or 15.

TABLE 2

Examples 8–13 - Commercial Catalysts

| Ex. Nr. | CHARACTERISTICS OF THE CATALYST | PRODUCER |
|---|---|---|
| 8 | Zeolite: Y<br>Name: H-SUSY ZEOLYST ™ CBV600<br>$SiO_2/Al_2O_3$ ratio: 5.2 mole/mole<br>Form: extruded diameter 1/16"<br>Treatment before catalytic test:<br>grinding to 14–35 mesh | Zeolyst |
| 9 | Zeolite: Y<br>Name: H-SDUSY ZEOLYST ™ CBV720<br>$SiO_2/Al_2O_3$ ratio: 30 mole/mole<br>Form: powder<br>Treatment before catalytic test:<br>as described in Example 14 | Zeolyst |
| 10 | Zeolite: Y<br>Name: H-SDUSY ZEOLYST ™ CBV780<br>$SiO_2/Al_2O_3$ ratio: 80 mole/mole<br>Form: powder<br>Treatment before catalytic test:<br>as described in Example 14 | Zeolyst |
| 11 | Zeolite: Y<br>Name: H-SDUSY ZEOLYST ™ CBV901<br>$SiO_2/Al_2O_3$ ratio: 80 mole/mole<br>Form: powder<br>Treatment before catalytic test:<br>as described in Example 14 | Zeolyst |
| 12 | Zeolite: Mordenite<br>Name: Ammonium Mordenite<br>ZEOLYST ™ CBV21A<br>$SiO_2/Al_2O_3$ ratio: 20 mole/mole<br>Form: powder<br>Treatment before catalytic test:<br>as described in Example 15 | Zeolyst |
| 13 | Zeolite: Y<br>Name: HSZ-330HUD Tosoh<br>Molar ratios $SiO_2/Al_2O_3$: 6.18,<br>Na/Al = 0.02<br>Form: extruded diameter 1.5 mm<br>(wt ratio zeolite/clay = 100:25)<br>Treatment before catalytic test:<br>grinding to 14–35 mesh | Tosoh |

In the examples which specify the catalytic activity results, it is indicated with its commercial name.

Example 14—Granulation Treatment of the Catalyst 10 g of zeolite are dispersed in about 20 g of demineralized water, the water is slowly evaporated, under stirring with a magnetic anchor, the sample is dried at 120° C. and calcined at 350° C. for 4 hours. The sample is granulated to a size of 14–35 mesh.

Example 15—Granulation Treatment of the Catalyst 30 g of zeolite are calcined at 550° C. for 4 hours, and subsequently dispersed in about 60 g of demineralized water, the water is slowly evaporated, under stirring with a magnetic anchor, the sample is dried at 120° C. and calcined at 350° C. for 4 hours. The sample is granulated to a size of 14–35 mesh.

Examples of Catalytic Performances

The catalytic activity tests described in the following examples were carried out in an experimental laboratory apparatus, in which it is possible to study the best operating conditions to be adopted for the process.

Pseudo-cumene with a titer of >99% by weight, was fed for the tests, the composition of the feeding mixture used is indicated in Table 3 below, wherein $\Sigma$<C8 are compounds having a lower molecular weight than xylenes, $\Sigma$C8 are xylenes, 135TMB is mesitylene, 124TMB is pseudo-cumene, 123TMB is hemimellitene, 1245TeMB is durene, 1235TeMB is isodurene, 1234TeMB is prenitene, $\Sigma$>C10 are compounds having a higher molecular weight than $C_{10}$ isomers.

TABLE 3

| Composition of feeding mixture (weight %) | | | | | | | | |
|---|---|---|---|---|---|---|---|---|
| $\Sigma$ < C8 | $\Sigma$ C8 | 135 TMB | 124 TMB | 123 TMB | 1245 TeMB | 1235 TeMB | 1234 TeMB | $\Sigma$ > C10 |
| 0.2 | 0.0 | 0.1 | 99.2 | 0.1 | 0.0 | 0.0 | 0.0 | 0.0 |

The equipment and operating procedure are described below.

CATALYTIC TEST: Equipment and Operating Procedure

The isomerization and transalkylation reactions of pseudo-cumene are carried out in a fixed bed tubular microreactor having the following characteristics: material= AISI 316L stainless steel, length 180 mm, $\emptyset_{int}$=12 mm, thermocouple sheath with $\emptyset_{ext}$=3 mm. The reactor is placed in an oven which allows it to be brought to the temperature selected for the reaction.

The catalyst used for the test has a size of <2 mm; when one of the commercial catalysts described above, produced in an industrial size, is tested, it is previously reduced to the desired dimensions. The catalyst charge is 2÷8 g and it is positioned in the reactor between two layers of granular quartz.

The feed is preheated before being charged into the lower part of the reactor and before it comes into contact with the catalyst; the flow-rate is dosed with a pump of the HPLC type.

The pressure of the plant is controlled by a regulating valve situated at the outlet of the reactor.

The mixture of effluent hydrocarbons from the pressure regulating valve is cooled and samples of reaction raw product are collected to evaluate the catalytic performances.

The samples are analyzed by means of gaschromatography and the catalytic performances are evaluated by calculating the composition of the mixture, the ratios between the isomers, the conversion and yield to the two compounds of interest.

The regeneration of the catalyst after the activity test was effected in the same reactor used for the reaction. The operating conditions are as follows: temperature=450÷550° C., pressure=1÷3 bar, oxygen concentration=0.1÷20% and GHSV space velocity=3000÷6000 hours$^{-1}$. In particular, the treatment begins with a stream of nitrogen alone to which an equal flow of air is progressively added (in about 1 hour), the nitrogen stream is subsequently progressively reduced until it is annulled (in about 1 hour) and the treatment is prolonged for 5 to 24 hours, depending on the duration of the previous activity test. At the end of the treatment, the reactor is washed with a stream of nitrogen and the catalytic activity test can be repeated.

Examples 16–35—Activity Test

Catalytic activity examples are described hereunder, with catalysts based on different zeolitic structures and with catalysts used after being subjected to rejuvenation treatment following a previous reaction phase. The results obtained in a duration test with one of the catalysts having the characteristics of the present invention, are also provided.

Tables 4–14 below indicate the catalytic performances obtained with different types of zeolitic structures, prepared according to what is previously described in Examples 1–15.

The operating conditions maintained in the test are indicated in the same Tables 4–14.

Table 4 specifies the results obtained with a catalyst based on beta zeolite, obtained as indicated in Example 1. The results demonstrate that this catalyst can be advantageously used for the purposes of the present invention.

TABLE 4

Examples 16/1–16/2

| OPERATING CONDITIONS | |
|---|---|
| Catalyst | Beta zeolite/100, See Example 1 |
| Reaction temperature (° C.) | 250–350 |
| WHSV (h$^{-1}$) | 8.0 |
| Pressure (bar) | 50 |
| Feeding mixture | See Table 3 |

| | | CATALYTIC PERFORMANCES | | | | | | | | |
|---|---|---|---|---|---|---|---|---|---|---|
| | React. | Composition of the reaction raw product (molar %) | | | | | | | | |
| Ex. Nr. | temp (° C.) | $\Sigma$ < C8 | $\Sigma$ C8 | 135 TMB | 124 TMB | 123 TMB | 1245 TeMB | 1235 TeMB | 1234 TeMB | $\Sigma$ > C10 |
| 16/1 | 250 | 0.9 | 12.4 | 20.3 | 45.8 | 5.7 | 6.0 | 6.6 | 1.4 | 0.5 |
| 16/2 | 350 | 3.5 | 18.6 | 12.0 | 32.4 | 4.5 | 9.4 | 11.3 | 2.9 | 5.1 |

In the activation phase of the activity test, the catalyst is heated to the reaction temperature in a stream of dry nitrogen, at low pressure, for 1 hour. The feeding of pseudo-cumene is then initiated.

Table 5 indicates the results obtained with a catalyst based on ZSM-12 obtained according to what is described in Example 3.

TABLE 5

Examples 17/1–17/5

OPERATING CONDITIONS

| Catalyst | ZSM-12, See Example 3 |
|---|---|
| Reaction temperature (° C.) | 280–380 |
| WHSV (h$^{-1}$) | 4.33 |
| Pressure (bar) | 33.4 |
| Feeding mixture | See Table 3 |

CATALYTIC PERFORMANCES

| | React. | Composition of the reaction raw product (molar %) | | | | | | | |
|---|---|---|---|---|---|---|---|---|---|
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 17/1 | 280 | 0.3 | 5.7 | 24.1 | 56.3 | 7.2 | 2.3 | 2.7 | 0.6 | 0.3 |
| 17/2 | 300 | 0.4 | 6.8 | 23.2 | 55.4 | 7.3 | 2.7 | 3.2 | 0.7 | 0.2 |
| 17/3 | 325 | 1.2 | 14.8 | 18.0 | 43.7 | 6.0 | 6.1 | 7.6 | 1.8 | 0.8 |
| 17/4 | 350 | 2.9 | 20.5 | 13.4 | 34.0 | 4.8 | 8.6 | 11.0 | 2.6 | 1.6 |
| 17/5 | 380 | 2.4 | 18.6 | 15.0 | 37.4 | 5.4 | 7.5 | 9.8 | 2.4 | 1.2 |

Table 6 indicates the results obtained with a catalyst based on NU-88 obtained according to what is described in Example 4.

TABLE 6

Examples 18/1–18/6

OPERATING CONDITIONS

| Catalyst | NU-88, See Example 4 |
|---|---|
| Reaction temperature (° C.) | 300–425 |
| WHSV (h$^{-1}$) | 4.33 |
| Pressure (bar) | 33 |
| Feeding mixture | See Table 3 |

CATALYTIC PERFORMANCES

| | React. | Composition of the reaction raw product (molar %) | | | | | | | |
|---|---|---|---|---|---|---|---|---|---|
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 18/1 | 300 | 0.2 | 1.3 | 9.1 | 80.7 | 7.1 | 0.6 | 0.7 | 0.2 | 0.1 |
| 18/2 | 325 | 3.0 | 20.1 | 13.6 | 33.4 | 4.6 | 9.0 | 11.4 | 2.6 | 2.2 |
| 18/3 | 350 | 3.9 | 21.6 | 11.7 | 29.9 | 4.2 | 9.7 | 12.4 | 3.0 | 3.2 |
| 18/4 | 380 | 2.9 | 19.3 | 14.7 | 36.2 | 5.2 | 7.7 | 9.9 | 2.4 | 1.1 |
| 18/5 | 400 | 1.5 | 15.0 | 17.8 | 43.0 | 6.1 | 5.7 | 7.4 | 1.8 | 1.2 |
| 18/6 | 425 | 3.9 | 21.9 | 12.5 | 32.5 | 4.6 | 8.8 | 11.6 | 2.9 | 1.3 |

Table 7 indicates the results obtained with a catalyst based on Mazzite obtained according to what is described in Example 5.

TABLE 7

Examples 19/1–19/3

OPERATING CONDITIONS

| Catalyst | Mazzite, See Example 5 |
|---|---|
| Reaction temperature (° C.) | 300–350 |
| WHSV (h$^{-1}$) | 4.33 |
| Pressure (bar) | 33 |
| Feeding mixture | See Table 3 |

TABLE 7-continued

Examples 19/1–19/3

CATALYTIC PERFORMANCES

| | React. | Composition of the reaction raw product (molar %) | | | | | | | | |
|---|---|---|---|---|---|---|---|---|---|---|
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 19/1 | 300 | 0.8 | 11.9 | 20.1 | 48.0 | 6.4 | 5.0 | 6.1 | 1.3 | 0.4 |
| 19/2 | 325 | 2.0 | 17.8 | 15.8 | 38.2 | 5.2 | 7.6 | 9.5 | 2.2 | 1.1 |
| 19/3 | 350 | 3.3 | 21.2 | 13.0 | 32.6 | 4.6 | 9.0 | 11.6 | 2.7 | 1.6 |

Table 8 indicates the results obtained with a catalyst based on MCM-22 obtained according to what is described in Example 6.

TABLE 8

Examples 20/1–20/4

OPERATING CONDITIONS

| | |
|---|---|
| Catalyst | MCM-22, See Example 6 |
| Reaction temperature (° C.) | 280–350 |
| WHSV (h$^{-1}$) | 4.33 |
| Pressure (bar) | 33 |
| Feeding mixture | See Table 3 |

CATALYTIC PERFORMANCES

| | React. | Composition of the reaction raw product (molar %) | | | | | | | | |
|---|---|---|---|---|---|---|---|---|---|---|
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 20/1 | 280 | 0.3 | 4.0 | 23.0 | 60.8 | 7.9 | 1.5 | 1.8 | 0.4 | 0.2 |
| 20/2 | 300 | 0.6 | 8.3 | 22.2 | 53.0 | 7.1 | 3.3 | 4.1 | 0.9 | 0.4 |
| 20/3 | 325 | 1.6 | 15.0 | 17.5 | 43.0 | 5.9 | 6.1 | 7.8 | 1.8 | 0.8 |
| 20/4 | 350 | 2.9 | 19.4 | 14.0 | 35.3 | 5.0 | 8.1 | 10.4 | 2.4 | 1.9 |

Table 9 indicates the results obtained with a catalyst based on ERS-10 obtained according to what is described in Example 7.

TABLE 9

Examples 21/1–21/2

OPERATING CONDITIONS

| | |
|---|---|
| Catalyst | ERS-10, See Example 7 |
| Reaction temperature (° C.) | 350–380 |
| WHSV (h$^{-1}$) | 4.33 |
| Pressure (bar) | 33 |
| Feeding mixture | See Table 3 |

CATALYTIC PERFORMANCES

| | React. | Composition of the reaction raw product (molar %) | | | | | | | | |
|---|---|---|---|---|---|---|---|---|---|---|
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 21/1 | 350 | 0.4 | 6.4 | 18.2 | 59.4 | 8.6 | 2.5 | 2.9 | 0.7 | 0.4 |
| 21/2 | 380 | 0.7 | 9.2 | 16.2 | 55.6 | 8.1 | 3.6 | 4.4 | 1.1 | 0.6 |

Tables 10–13 indicate the results obtained with various kinds of commercial zeolite-based catalysts of the FAU type, whose fundamental characteristics are specified in Table 2. The results show that all of these catalysts can be advantageously used for the purposes of the present invention.

TABLE 10

Examples 22/1–22/1

OPERATING CONDITIONS

| Catalyst | Zeolite H-SUSY ZEOLYST ™ CBV600, See Example 8 |
|---|---|
| Reaction temperature (° C.) | 275–350 |
| WHSV (h⁻¹) | 12.0 |
| Pressure (bar) | 50 |
| Feeding mixture | See Table 3 |

CATALYTIC PERFORMANCES

| | React. | Composition of the reaction raw product (molar %) | | | | | | | | |
|---|---|---|---|---|---|---|---|---|---|---|
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 22/1 | 275 | 2.2 | 20.0 | 10.5 | 37.1 | 4.1 | 10.1 | 10.8 | 2.5 | 2.3 |
| 22/2 | 350 | 3.6 | 20.3 | 11.8 | 30.2 | 4.3 | 9.9 | 11.9 | 3.1 | 4.5 |

TABLE 11

Example 23/1

OPERATING CONDITIONS

| Catalyst | Zeolite H-SDUSY ZEOLYST ™ CBV720, See Example 9 |
|---|---|
| Reaction temperature (° C.) | 275 |
| WHSV (h⁻¹) | 8.0 |
| Pressure (bar) | 50 |
| Feeding mixture | See Table 3 |

CATALYTIC PERFORMANCES

| | React. | Composition of the reaction raw product (molar %) | | | | | | | | |
|---|---|---|---|---|---|---|---|---|---|---|
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 23/1 | 275 | 2.2 | 19.7 | 11.8 | 37.9 | 4.0 | 9.5 | 10.3 | 2.3 | 1.9 |

TABLE 12

Example 24/1

OPERATING CONDITIONS

| Catalyst | Zeolite H-SDUSY ZEOLYST ™ CBV780, See Example 10 |
|---|---|
| Reaction temperature (° C.) | 300 |
| WHSV (h⁻¹) | 8.0 |
| Pressure (bar) | 50 |
| Feeding mixture | See Table 3 |

CATALYTIC PERFORMANCES

| | React. | Composition of the reaction raw product (molar %) | | | | | | | | |
|---|---|---|---|---|---|---|---|---|---|---|
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 24/1 | 300 | 2.1 | 20.6 | 12.5 | 35.7 | 4.5 | 9.2 | 10.4 | 2.5 | 2.2 |

TABLE 13

Example 25/1

OPERATING CONDITIONS

| Catalyst | Zeolite H-SDUSY ZEOLYST ™ CBV905, See Example 11 |
| --- | --- |
| Reaction temperature (° C.) | 325 |
| WHSV (h⁻¹) | 8.0 |
| Pressure (bar) | 50 |
| Feeding mixture | See Table 3 |

CATALYTIC PERFORMANCES

| | React. | Composition of the reaction raw product (molar %) | | | | | | | | |
| --- | --- | --- | --- | --- | --- | --- | --- | --- | --- | --- |
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 25/1 | 325 | 1.9 | 19.5 | 12.6 | 36.3 | 4.6 | 9.3 | 10.8 | 2.7 | 1.9 |

Table 14 indicates the results obtained with a catalyst based on mordenite, whose fundamental characteristics are specified in Table 2. Also in this case, the results show that this catalyst can be used for the purposes of the present invention.

TABLE 14

Examples 26/1–26/2

OPERATING CONDITIONS

| Catalyst | Mordenite ZEOLYST ™ CBV21A See Example 12 |
| --- | --- |
| Reaction temperature (° C.) | 275-325 |
| WHSV (h⁻¹) | 8.0 |
| Pressure (bar) | 50 |
| Feeding mixture | See Table 3 |

CATALYTIC PERFORMANCES

| | React. | Composition of the reaction raw product (molar %) | | | | | | | | |
| --- | --- | --- | --- | --- | --- | --- | --- | --- | --- | --- |
| Ex. Nr. | temp (° C.) | Σ < C8 | Σ C8 | 135 TMB | 124 TMB | 123 TMB | 1245 TeMB | 1235 TeMB | 1234 TeMB | Σ > C10 |
| 26/1 | 275 | 1.1 | 15.2 | 15.4 | 45.7 | 5.8 | 6.5 | 7.2 | 1.6 | 1.0 |
| 26/2 | 325 | 3.8 | 20.3 | 12.1 | 30.3 | 4.4 | 9.9 | 11.9 | 3.1 | 3.8 |

Examples 27–31—Duration and Regeneration Tests of the Catalyst

Tables 15–18 below indicate the catalytic performances obtained in a duration test of 5,500 hours with the catalyst based on Beta zeolite, at 50% of active phase, prepared according to what is described in Example 2.

The operating conditions maintained in the test are indicated in the same Tables 15–18.

In the test, 1,2,4-trimethylbenzene was fed, with a titer >99% by weight, whose composition is indicated in Table 3.

The examples of Table 15 provide the results obtained in the first phase of the test, effected at a temperature of 275° C. A slow progressive deterioration in the catalytic activity can be observed, due to the formation of high-boiling organic substances and their deposit on the catalyst. As an index of the catalytic activity, in particular the concentration of the residual 1,2,4-trimethylbenzene can be observed, which moves from 36.9 to 82.3%, passing from the 20th hour to the 1806$^{th}$ hour of the operating period.

TABLE 15

Examples 27/1–27/6

OPERATING CONDITIONS

| Catalyst | Zeolite Beta/50, See Example 2 |
|---|---|
| Reaction temperature (° C.) | 275 |
| WHSV (h$^{-1}$) | 4.0 |
| Pressure (bar) | 40 |
| Feeding mixture | See Table 3 |

CATALYTIC PERFORMANCES

Composition of the reaction raw product (molar %)

| Ex. Nr. | TOS (h) | Σ < C8 | Σ C8 | 135 TMB | 124 TMB | 123 TMB | 1245 TeMB | 1235 TeMB | 1234 TeMB | Σ > C10 |
|---|---|---|---|---|---|---|---|---|---|---|
| 27/1 | 20 | 2.3 | 18.5 | 16.3 | 36.9 | 4.7 | 8.5 | 9.6 | 2.1 | 0.8 |
| 27/2 | 397 | 1.3 | 14.7 | 18.5 | 41.3 | 5.4 | 7.4 | 8.4 | 1.9 | 0.8 |
| 27/3 | 718 | 0.9 | 11.5 | 20.1 | 49.0 | 6.3 | 4.9 | 5.4 | 1.2 | 0.6 |
| 27/4 | 1106 | 0.3 | 6.0 | 17.1 | 62.4 | 7.3 | 2.7 | 2.8 | 0.7 | 0.3 |
| 27/5 | 1393 | 0.2 | 3.8 | 9.3 | 75.5 | 6.1 | 1.8 | 1.8 | 0.4 | 0.5 |
| 27/6 | 1806 | 0.2 | 1.7 | 7.0 | 82.3 | 4.9 | 1.4 | 1.4 | 0.3 | 0.2 |

The examples of Table 16 provide the results obtained in a subsequent phase of the test, carried out operating at a temperature of 320° C. In addition to the greater catalytic activity, they show a progressive recovery of the activity itself, as a result of the gradual removal of the high-boiling organic substances deposited on the catalyst due to the compounds present in the reactor, the reaction products and residual reagent. This is net of the contribution of other substances which can be formed at a higher temperature. On observing the concentration of residual 1,2,4-trimethylbenzene, for example, it can be seen that this moves from 47.1 to 39.0 and subsequently to 38.1%, proceeding from the 1876$^{th}$ to the 2112$^{th}$ and subsequently to the 2474$^{th}$ hour of the operating period.

In order to quantify the aging state of the catalyst in a reference condition, during the phase at 320° C., the reaction temperature was brought back from time to time and for short periods to 275° C., the temperature used in the first phase of the test. The results are provided in Table 17 and are a good indication of the progressive reactivation of the catalyst. On observing the concentration of residual 1,2,4-trimethylbenzene, in fact, it can be seen that it passes from the original value of 82.3% at the 1806$^{th}$ hour to 64.0% at the 2027$^{th}$ hour and to 60.0% at the 2216$^{th}$ hour of the operating period, as a result of having operated at a temperature of 320° C. in the intermediate periods.

TABLE 16

Examples 28/1–28/3

OPERATING CONDITIONS

| Catalyst | Zeolite Beta/50, See Example 2 |
|---|---|
| Reaction temperature (° C.) | 320 |
| WHSV (h$^{-1}$) | 4.0 |
| Pressure (bar) | 40 |
| Feeding mixture | See Table 3 |

CATALYTIC PERFORMANCES

Composition of the reaction raw product (molar %)

| Ex. Nr. | TOS (h) | Σ < C8 | Σ C8 | 135 TMB | 124 TMB | 123 TMB | 1245 TeMB | 1235 TeMB | 1234 TeMB | Σ > C10 |
|---|---|---|---|---|---|---|---|---|---|---|
| 28/1 | 1876 | 0.5 | 9.6 | 17.3 | 47.1 | 6.0 | 7.4 | 8.5 | 2.1 | 1.1 |
| 28/2 | 2112 | 1.8 | 16.8 | 16.6 | 39.0 | 5.3 | 7.8 | 9.1 | 2.2 | 0.9 |
| 28/3 | 2474 | 2.1 | 17.7 | 16.1 | 38.1 | 5.2 | 7.9 | 9.2 | 2.2 | 1.1 |

TABLE 17

Examples 29/1–29/2

OPERATING CONDITIONS

| | |
|---|---|
| Catalyst | Zeolite Beta/50, See Example 2 |
| Reaction temperature (° C.) | 275 |
| WHSV (h$^{-1}$) | 4.0 |
| Pressure (bar) | 40 |
| Feeding mixture | See Table 3 |

CATALYTIC PERFORMANCES
Estimation of the deactivation at the temperature of 275° C. (*)

| | | Composition of the reaction raw product (molar %) | | | | | | | | |
|---|---|---|---|---|---|---|---|---|---|---|
| Ex. Nr. | TOS (h) | Σ < C8 | Σ C8 | 135 TMB | 124 TMB | 123 TMB | 1245 TeMB | 1235 TeMB | 1234 TeMB | Σ > C10 |
| 29/1 | 2027 | 0.4 | 5.7 | 15.5 | 64.0 | 7.6 | 2.6 | 2.9 | 0.7 | 0.3 |
| 29/2 | 2216 | 0.4 | 6.5 | 17.6 | 60.0 | 7.6 | 2.9 | 3.2 | 0.8 | 0.5 |

(*) During the test at 320° C. the reaction temperature is brought to 275° C. for about 10 hours in order to verify the catalytic activity under the same conditions as the first phase of the duration test The first cycle of the duration test was prolonged for 5,000 hours without ever regenerating the catalyst.

Table 18 below indicates the catalytic performances obtained with the catalyst based on Beta zeolite, at 50% of active phase, prepared according to what is described in Example 2, after regeneration. The regeneration was effected with the procedure described above in the paragraph dedicated to the operating procedure of the catalytic test (in particular, the temperature was maintained at 480° C., the pressure at 1 bar, the GHSV at 3,000 hours$^{-1}$ and the treatment was prolonged for 12 hours). In the results in Table 18, the performances reached with the fresh catalyst, obtained from the start of the test, are compared with those obtained after regeneration, at the end of the first cycle of 5,000 hours of the duration test: the complete recovery of the performance is evident.

TABLE 18

Examples 30/1–30/7

OPERATING CONDITIONS

| | |
|---|---|
| Catalyst | Zeolite Beta/50, See Example 2 |
| Reaction temperature (° C.) | 275 |
| WHSV (h$^{-1}$) | 4.0 |
| Pressure (bar) | 40 |
| Feeding mixture | See Table 3 |

CATALYTIC PERFORMANCES WITH FRESH CATALYST

| | | Composition of the reaction raw product (molar %) | | | | | | | | |
|---|---|---|---|---|---|---|---|---|---|---|
| Ex. Nr. | TOS (h) | Σ < C8 | Σ C8 | 135 TMB | 124 TMB | 123 TMB | 1245 TeMB | 1235 TeMB | 1234 TeMB | Σ > C10 |
| 30/1 | 5 | 2.1 | 18.1 | 16.7 | 37.7 | 4.8 | 8.3 | 9.3 | 2.0 | 0.7 |
| 30/2 | 112 | 1.8 | 16.5 | 17.1 | 38.2 | 5.0 | 8.4 | 9.4 | 2.1 | 1.0 |
| 30/3 | 323 | 1.5 | 15.2 | 18.2 | 40.6 | 5.3 | 7.6 | 8.5 | 1.9 | 0.8 |
| 30/4 | 4695 | 0.3 | 3.6 | 14.8 | 68.7 | 7.8 | 1.8 | 1.9 | 0.5 | 0.3 |

CATALYTIC PERFORMANCES WITH REGENERATED CATALYST

| | | Composition of the reaction raw product (molar %) | | | | | | | | |
|---|---|---|---|---|---|---|---|---|---|---|
| Ex. Nr. | TOS (h) | Σ < C8 | Σ C8 | 135 TMB | 124 TMB | 123 TMB | 1245 TeMB | 1235 TeMB | 1234 TeMB | Σ > C$_{10}$ |
| 30/5 | 5000 + 4 | 2.1 | 17.0 | 15.5 | 37.4 | 4.8 | 9.1 | 10.2 | 2.3 | 1.3 |
| 30/6 | 5000 + 101 | 1.8 | 16.4 | 17.0 | 38.3 | 5.0 | 8.5 | 9.5 | 2.2 | 1.0 |
| 30/7 | 5000 + 317 | 1.6 | 15.4 | 17.3 | 39.7 | 5.2 | 8.2 | 9.2 | 2.1 | 1.1 |

Table 19 below indicates the catalytic performances obtained in a duration test of 1,151 hours using the commercial catalyst based on Y zeolite (80% of active phase), whose characteristics are specified in Example 15. The operating conditions maintained in the test are indicated in the same Table 19.

During the test period only a negligible deterioration was observed, passing from an initial molar concentration of residual 1,2,4-trimethylbenzene of 40.1% to a final concentration of 43.4%, maintaining a constant molar ratio of the two compounds of interest close to 1. After 475 hours of test, a regeneration of the catalyst was effected, operating in the same reactor used for the reaction.

The regeneration was carried out with the procedure described above in the paragraph dedicated to the operating procedure of the catalytic test, (in particular, the temperature was maintained at 550° C., the pressure at 1 bar, the GHSV at 3,000 hours$^{-1}$ and the treatment was prolonged for 16 hours).

At the end of the treatment, the reactor was washed with a stream of nitrogen and the catalytic activity test was restarted.

Examples 32–35—Recycling of Poor-quality Isomers and Variation in the Production Ratio Between Mesitylene and Durene Tables 20–23 below indicate the catalytic performances obtained with the catalyst based on Beta zeolite, at 50% of active phase, prepared according to what is described in Example 2, by feeding mixtures of pseudo-cumene with hydro-carbon fractions having a varying composition, obtained from the reaction raw product obtained during the same test and fractionated into its components by distillation and crystallization.

Table 20 relates to the recycling of 1,2,3-trimethylbenzene together with pseudo-cumene.

TABLE 19

Examples 31/1–31/16

OPERATING CONDITIONS

| Catalyst | Y 330 HUD, See Example 15 |
|---|---|
| Reaction temperature (° C.) | 245 |
| WHSV (h$^{-1}$) | 3.24 |
| Pressure (bar) | 33 |
| Feeding mixture | See Table 3 |

CATALYTIC PERFORMANCES WITH FRESH CATALYST

Composition of the reaction raw product (molar %)

| Ex. Nr. | TOS (h) | Σ < C8 | Σ C8 | 135 TMB | 124 TMB | 123 TMB | 1245 TeMB | 1235 TeMB | 1234 TeMB | Σ > C10 |
|---|---|---|---|---|---|---|---|---|---|---|
| 31/1 | 126 | 1.5 | 21.3 | 9.7 | 40.1 | 3.9 | 9.7 | 10.4 | 2.0 | 1.4 |
| 31/2 | 191 | 1.5 | 21.3 | 9.8 | 40.1 | 3.9 | 9.6 | 10.4 | 2.0 | 1.2 |
| 31/3 | 285 | 1.4 | 21.1 | 9.6 | 40.8 | 3.9 | 9.6 | 10.2 | 2.0 | 1.1 |
| 31/4 | 328 | 1.4 | 21.2 | 9.7 | 40.8 | 3.9 | 9.5 | 10.2 | 2.0 | 1.2 |
| 31/5 | 348 | 1.4 | 21.1 | 9.7 | 41.0 | 3.9 | 9.5 | 10.1 | 2.0 | 1.3 |

CATALYTIC PERFORMANCES WITH REGENERATED CATALYST

Composition of the reaction raw product (molar %)

| Ex. Nr. | TOS (h) | Σ < C8 | Σ C8 | 135 TMB | 124 TMB | 123 TMB | 1245 TeMB | 1235 TeMB | 1234 TeMB | Σ > C$_{10}$ |
|---|---|---|---|---|---|---|---|---|---|---|
| 31/6 | 481 | 2.0 | 21.9 | 9.9 | 37.5 | 3.8 | 10.2 | 11.1 | 2.2 | 1.4 |
| 31/7 | 575 | 1.4 | 21.3 | 9.3 | 41.2 | 3.9 | 9.6 | 10.1 | 2.0 | 1.2 |
| 31/8 | 595 | 1.4 | 21.2 | 9.4 | 41.1 | 3.9 | 9.5 | 10.1 | 2.0 | 1.3 |
| 31/9 | 646 | 1.4 | 21.5 | 9.6 | 40.2 | 3.9 | 9.5 | 10.1 | 2.0 | 1.2 |
| 31/10 | 771 | 1.3 | 20.9 | 9.4 | 41.3 | 3.9 | 9.5 | 10.1 | 2.0 | 1.2 |
| 31/11 | 816 | 1.4 | 21.0 | 9.4 | 41.6 | 3.9 | 9.5 | 10.0 | 2.0 | 1.2 |
| 31/12 | 909 | 1.2 | 20.6 | 9.1 | 43.0 | 3.9 | 9.3 | 9.7 | 1.9 | 1.1 |
| 31/13 | 962 | 1.2 | 20.7 | 9.2 | 42.7 | 3.9 | 9.1 | 9.6 | 1.9 | 1.1 |
| 31/14 | 1077 | 1.3 | 21.3 | 9.2 | 43.2 | 3.9 | 8.9 | 9.3 | 1.8 | 1.0 |
| 31/15 | 1125 | 1.3 | 21.2 | 9.1 | 43.3 | 3.9 | 8.9 | 9.3 | 1.8 | 1.0 |
| 31/16 | 1151 | 1.3 | 21.5 | 9.2 | 43.4 | 3.9 | 8.7 | 9.1 | 1.8 | 0.9 |

TABLE 20

Example 32/1

OPERATING CONDITIONS

| Catalyst | Zeolite Beta/50, See Example 2 |
|---|---|
| Reaction temperature (° C.) | 310 |
| WHSV (h⁻¹) | 4.1 |
| Pressure (bar) | 30 |

Composition of the feeding mixture (molar %)

| Σ < C8 | Σ C8 | 135 TMB | 124 TMB | 123 TMB | 1245 TeMB | 1235 TeMB | 1234 TeMB | Σ > C10 |
|---|---|---|---|---|---|---|---|---|
| 0.0 | 0.3 | 2.7 | 84.9 | 11.2 | 0.2 | 0.2 | 0.0 | 0.0 |

CATALYTIC PERFORMANCES

Composition of the reaction raw product (molar %)

| Ex. Nr. | TOS (h) | Σ < C8 | Σ C8 | 135 TMB | 124 TMB | 123 TMB | 1245 TeMB | 1235 TeMB | 1234 TeMB | Σ > $C_{10}$ |
|---|---|---|---|---|---|---|---|---|---|---|
| 32/1 | 1258 | 0.5 | 9.0 | 21.2 | 52.1 | 7.1 | 3.9 | 4.5 | 1.1 | 0.3 |

Table 21 relates to the recycling of 1,2,3,5-tetramethylbenzene together with pseudo-cumene.

TABLE 21

Examples 33/1

OPERATING CONDITIONS

| Catalyst | Zeolite Beta/50, See Example 2 |
|---|---|
| Reaction temperature (° C.) | 320 |
| WHSV (h⁻¹) | 3.7 |
| Pressure (bar) | 50 |

Composition of the feeding mixture (molar %)

| Σ < C8 | Σ C8 | 135 TMB | 124 TMB | 123 TMB | 1245 TeMB | 1235 TeMB | 1234 TeMB | Σ > C10 |
|---|---|---|---|---|---|---|---|---|
| 0.0 | 0.0 | 0.3 | 86.6 | 0.2 | 2.3 | 10.1 | 0.0 | 0.0 |

CATALYTIC PERFORMANCES

Composition of the reaction raw product (molar %)

| Ex. Nr. | TOS (h) | Σ < C8 | Σ C8 | 135 TMB | 124 TMB | 123 TMB | 1245 TeMB | 1235 TeMB | 1234 TeMB | Σ > $C_{10}$ |
|---|---|---|---|---|---|---|---|---|---|---|
| 33/1 | 1737 | 0.8 | 10.8 | 16.6 | 39.9 | 5.5 | 10.6 | 11.9 | 2.6 | 0.9 |

Table 22 relates to the recycling of 1,2,3-trimethylbenzene and 1,2,3,5-tetramethylbenzene together with pseudo-cumene.

TABLE 22

Example 34/1

OPERATING CONDITIONS

| Catalyst | Zeolite Beta/50, See Example 2 |
|---|---|
| Reaction temperature (° C.) | 320 |
| WHSV (h⁻¹) | 4.3 |
| Pressure (bar) | 50 |

TABLE 22-continued

Example 34/1

Composition of the feeding mixture (molar %)

| Σ < C8 | Σ C8 | 135 TMB | 124 TMB | 123 TMB | 1245 TeMB | 1235 TeMB | 1234 TeMB | Σ > C10 |
|---|---|---|---|---|---|---|---|---|
| 0.0 | 0.0 | 0.1 | 85.0 | 8.5 | 1.6 | 4.5 | 0.0 | 0.0 |

CATALYTIC PERFORMANCES

Composition of the reaction raw product (molar %)

| Ex. Nr. | TOS (h) | Σ < C8 | Σ C8 | 135 TMB | 124 TMB | 123 TMB | 1245 TeMB | 1235 TeMB | 1234 TeMB | Σ > $C_{10}$ |
|---|---|---|---|---|---|---|---|---|---|---|
| 34/1 | 2587 | 1.3 | 14.1 | 16.7 | 39.8 | 5.5 | 8.8 | 10.3 | 2.5 | 0.8 |

In addition to demonstrating the advantageous possibility of recycling the lower-exploitation $C_9$ and $C_{10}$ isomers, the results indicated in Tables 20–22 clearly show how it is possible with this method to control the production ratio of mesitylene/durene, a ratio which under the three different operating conditions varies from ~2 to ~5 mole/mole.

With a feeding consisting of pseudo-cumene alone, the mesitylene/durene production ratio can still be varied by acting on the operating conditions, in particular the temperature, as indicated in Table 23. The results show that a molar ratio mesitylene/durene ranging from ~2 to ~7, can be obtained.

TABLE 23

Examples 35/1–35/3

OPERATING CONDITIONS

| Catalyst | Zeolite Beta/50, See Example 2 |
|---|---|
| Reaction temperature (° C.) | 225–275 |
| WHSV ($h^{-1}$) | 4.0 |
| Pressure (bar) | 50 |
| Feeding mixture | See Table 3 |

CATALYTIC PERFORMANCES

| | | React. | Composition of the reaction raw product (molar %) | | | | | | | | |
|---|---|---|---|---|---|---|---|---|---|---|---|
| Ex. nr. | TOS (h) | temp (° C.) | Σ < C8 | Σ C8 | 135 TMB | 124 TMB | 123 TMB | 1245 TeMB | 1235 TeMB | 1234 TeMB | Σ > $C_{10}$ |
| 35/1 | 5034 | 225 | 0.3 | 5.4 | 19.6 | 60.1 | 7.3 | 2.8 | 3.0 | 0.8 | 0.4 |
| 35/2 | 5043 | 250 | 0.7 | 10.4 | 20.3 | 49.0 | 5.9 | 5.4 | 5.9 | 1.3 | 0.6 |
| 35/3 | 5087 | 275 | 1.7 | 16.2 | 16.9 | 38.5 | 4.9 | 8.5 | 9.6 | 2.2 | 1.1 |

What is claimed is:

1. A process for the preparation of a mixture comprising mesitylene and durene, said process comprising:
   treating pseudo-cumene with a catalytic composition at a temperature ranging from 210 to 450° C. and a pressure ranging from 1 to 50 bar to obtain said mixture comprising mesitylene and durene,
   wherein said catalytic composition comprises a zeolite,
   wherein said zeolite has a spaciousness index equal to or greater than 3,
   wherein said zeolite is in acid or prevalently acid form, and
   wherein said catalytic composition is not impregnated with one or more metals used for hydrogenation reactions.

2. The process according to claim 1, wherein said zeolite has a spaciousness index equal to or greater than 5.

3. The process according to claim 1, wherein said zeolite is at least one selected from the group consisting of beta zeolite, Y zeolite, ZSM-12 zeolite, MCM-22 zeolite, ERB-1, mazzite, mordenite, ZSM-20, L zeolite, ERS-10, Nu-1, Nu-88, offretite, and mixtures thereof.

4. The process according to claim 3, wherein said zeolite is a beta zeolite.

5. The process according to any of the previous claims, wherein said catalytic composition further comprises at least one binder selected from the group consisting of alumina, silica, magnesia, zirconia, and mixtures thereof.

6. The process according to claim 5, wherein said zeolite is beta zeolite and said catalytic composition has an extrazeolitic porosity consisting for a fraction of at least 25% of pores with a radius higher than 100 Å.

7. The process according to claim 6, wherein said catalytic composition has a total volume of extrazeolitic pores greater than or equal to 0.80 ml/g.

8. The process according to claim 1, wherein said zeolite has a molar ratio $SiO_2/Al_2O_3$ ranging from 4.5 to 4,000.

9. The process according to claim 8, wherein said molar ratio $SiO_2/Al_2O_3$ ranges from 4.5 to 400.

10. The process according to claim 1, wherein the temperature ranges from 225 to 400° C. and the pressure ranges from 5 to 50 bar.

11. The process according to claim 1, wherein said process is carried out in liquid phase.

12. The process according to claim 1, having a WHSV space velocity of from 0.1 to 20 hours$^{-1}$.

13. The process according to claim 1, wherein said process is carried out continuously in a fixed bed reactor.

14. The process according to claim 5, wherein the weight ratio between said zeolite and said binder ranges from 5:95 to 95:5.

15. The process according to claim 14, wherein said weight ratio ranges from 20:80 to 80:20.

16. The process according to claim 1, wherein the process temperature is gradually increased and when said catalytic composition shows at least partial deactivation, said catalytic composition is cyclically subjected to a rejuvenation process by increasing the temperature by at least 40° C. for a time ranging from 100 to 300 hours, and subsequently re-establishing the temperature conditions prior to the rejuvenation.

17. The process according to claim 1, further comprising:
distilling said mixture to separate a first fraction comprising xylene, a second fraction comprising non-converted pseudo-cumene, mesitylene and hemimellitene, a third fraction comprising durene, isodurene and prenitene, and a residue;
recovering said mesitylene from said second fraction by distillation and recovering said durene from said third fraction by crystallization.

18. The process according to claim 17, wherein said crystallization of durene from said third fraction is carried out without a solvent, at a temperature ranging from −20 to 10° C.

19. The process according to claim 18, wherein one or more crystals obtained from the crystallization are purified by washing with one or more alcohols or one or more light hydrocarbons.

20. The process according to claim 17, wherein pseudo-cumene and hemimellitene obtained from said distillation of said second fraction, are recycled to step (a).

21. The process according to claim 17, wherein said third fraction comprises isodurene and prenitene, and said isodurene and prenitene remaining in said third fraction after the crystallization of durene, are recycled to step (a).

22. The process according to claim 1, wherein hydrogen is not added during said process.

23. The process according to claim 1, wherein said catalytic composition consists essentially of said zeolite.

24. The process according to claim 1, wherein said catalytic composition consists essentially of said zeolite and a binder.

* * * * *